United States Patent [19]

Berry

[11] 4,281,362
[45] Jul. 28, 1981

[54] ELECTROSTATIC SHIELD FOR DIATHERMY TREATMENT HEAD

[75] Inventor: Fred M. Berry, Johnson County, Mo.

[73] Assignee: International Medical Electronics, Ltd., Kansas City, Mo.

[21] Appl. No.: 136,101

[22] Filed: Mar. 31, 1980

[51] Int. Cl.³ .............................................. A61N 1/06
[52] U.S. Cl. .................................. 361/437; 361/212; 128/804
[58] Field of Search ........................ 361/232, 212, 437; 128/804; 219/10.55 D

[56] References Cited

U.S. PATENT DOCUMENTS

| | | |
|---|---|---|
| 2,276,996 | 11/1942 | Milnowski . |
| 4,003,383 | 1/1977 | Brück .................................. 128/804 |
| 4,068,292 | 1/1978 | Berry et al. ....................... 128/804 X |
| 4,163,139 | 7/1979 | Malarkey et al. ..................... 361/212 |

FOREIGN PATENT DOCUMENTS

| | | |
|---|---|---|
| 2364970 | 7/1975 | Fed. Rep. of Germany ........... 128/804 |
| 7510644 | 3/1977 | Netherlands . |

Primary Examiner—J. D. Miller
Assistant Examiner—L. C. Schroeder
Attorney, Agent, or Firm—Lowe, Kokjer, Kircher, Wharton & Bowman

[57] ABSTRACT

This invention deals with an improved electrostatic shield which is adapted to be mounted on the applicator of a conventional diathermy apparatus between the radiating electrode thereof and the patient receiving treatment. The shield is comprised of a first and a second plurality of electrically conductive strips which form the body portion of the shield and which encircle the current carrying coil of the radiating electrode. The strips likewise form the face portion of the shield and define a plane which is generally parallel to the plane formed by the current carrying coil.

Each strip of the face portion is preferably coupled with one of the strips of the body portion. However, the face portion strips of the shield extend generally radially inward from the outer periphery of the surface defined by the face of the shield. These strips then terminate within the inner portion of the area defined by the shield such that the terminating end of the strips are electrically insulated from each other. A loop is provided to surround and electrically couple each of the strips of the body portion of the shield. In this configuration, the strips comprise an electrostatic shield which will impede electrostatic field radiated by the current carrying coil located within the applicator head. The shield, however, allows passage of the radiated electromagnetic field in a relatively unimpeded fashion.

5 Claims, 2 Drawing Figures

ELECTROSTATIC SHIELD FOR DIATHERMY TREATMENT HEAD

BACKGROUND AND BRIEF DESCRIPTION OF THE INVENTION

This invention relates to an electrostatic shield which is arranged to be incorporated into the applicator head of a conventional diathermy apparatus to effect the significant reduction of the electrostatic field radiated thereby.

Diathermy treatments involve the application of high frequency electric currents to body tissues. This technique utilizes the transcutaneous transmission of high frequency energy to the internal body tissues to be treated. The energy employed is sufficiently high to prevent adverse stimulation of nerves and muscles and is sufficiently low to prevent destruction of the treated tissue.

In a conventional diathermy apparatus, radio frequency electric currents are generated by the apparatus. These high frequency electric currents are then applied to the associated applicator which converts these high frequency currents into electromagnetic and electrostatic energy. The generated electromagnetic and electrostatic energy is then controllably applied by the applicator to the body of the patient. This energy causes heat to be generated within the internal body tissues which are within the radiating range of the applicator.

Painful heating of the subcutaneous fat layer and irritating skin burns may occur when a patient is treated using conventional diathermy apparatus. It has been found that the deleterious surface heating effects just described are primarily caused by electrostatic field radiated by conventional diathermy applicator head. The associated radiated electromagnetic field, however, does not cause the above-mentioned harmful burning of surface tissues. Furthermore, the radiated electromagnetic field penetrates deeply enough to provide relative heating in the muscle tissues without painful burning of the subcutaneous fat layer and skin tissue. This deep heating is at least partially produced because the electromagnetic field lines are tangential to the tissue interfaces rather than perpendicular and, as a result, the boundary conditions do not significantly effect or cause surface heating effects. As a result, the therapeutic deep heating benefits of diathermy treatment are primarily caused by the electromagnetic energy radiated by the applicator head.

By attenuating the electrostatic field radiated by the applicator head before it reaches the patient being treated, it is possible to virtually eliminate the above-described surface heating effects. A technique and apparatus for accomplishing this result are given and described in U.S. Pat. to Berry, et al, No. 4,068,292 entitled "Electrostatic Shield for Diathermy Treatment Head." This patent was issued on Jan. 10, 1978, and is incorporated by reference herein. The shield disclosed in that patent is comprised of a plurality of non-magnetic metallic (preferably copper) strips which are located interiorly of a coplanar, generally circular loop. Each of the strips is maintained at a generally perpendicular orientation with respect to the current carrying coil in the diathermy applicator head on which the shield is mounted. Each of the strips extends generally radially outward from the vicinity of the center of the loop and terminates at and is electrically connected with the circular loop.

It has been found that prior art applicator heads sometimes induce circulating currents in the circular loop of an associated shield. Other shields do not attenuate electrostatic energy which may be radiated outwardly through the sides of the applicator head. As a result, the outer casing of the applicator head prior art designs normally constructed of an electrically conductive material isolate the current carrying coils of the applicator head from external loads but permits circulating currents to be induced in the outer casing of the head.

In many instances the creation of circulating currents with the loop of the shield and the outer casing of the applicator head is highly undesirable and may be responsible for several detrimental effects. In particular circulating currents in the applicator produces an associated power loss which significantly reduces the operating efficiency of the diathermy apparatus. Another problem associated with such circulating currents within the outer casing of the applicator head is that same becomes extremely hot in response to such current flow therein. In fact, the outer casing of the head can become so hot that it is impossible to physically touch the head while the apparatus is in use. Accordingly, the minimization of such circulating currents with the outer casing of the applicator head and the circulating loop of the associated shield is highly desirable.

The present invention provides a unique electrostatic shield which overcomes the aforementioned problems. The electrostatic shield of the present invention includes a plurality of strips of the shield extending around the sides of the radiating coil within the applicator head and terminating the strips in a closed band which is located in a plane well below the coil. In the preferred embodiment of the invention, the shield is comprised of a side portion which encircles the radiating coil in the applicator head and a front portion which is positioned forwardly of the radiating coil. The side portion of the shield is comprised of a closed structure having a hollow interior. The walls of the structure are slotted to provide the plurality of lateral strips with same terminating in a closed band.

The forward or face portion of the shield is comprised of a plurality of nonmagnetic metallic strips which are arranged to extend radially inward from the periphery of the face so as to cover a majority of the surface area defined by the face portion of the shield. Each one of these strips is preferably electrically coupled with one and only one of the lateral strips which make up the side portion of the shield. In this way, each lateral strip and its associated face strips act as a single continuous strip which extend upwardly and which terminate within the area formed by the face portion of the shield.

As a result of this configuration, the electrostatic shield of the present invention provides improved attenuation of the electrostatic field which is radiated by the radiating coil of the applicator head. A primary benefit to be derived from this attenuation of the electrostatic field resides in the significant improvement in the operating efficiency of the diathermy apparatus. In particular, greater attenuation of the electrostatic field by the electrostatic shield of the present invention serves to further reduce electrostatic (capacitive) coupling between the treated body tissues and the applicator head. The reduction or elimination of capacitive coupling between the applicator head and body tissues, stablizes the operation of the diathermy apparatus and thereby reduces the likelihood that the applicator will be detuned from resonance upon an introduction of a load into the radiating region of the applicator head. By stablizing the operation of the diathermy apparatus, it becomes easier to keep the applicator head in electrical resonance thereby improving the accuracy of the power measuremens made by the device.

Use of the subject invention also enhances the operation of the diathermy apparatus by reducing head loss. As mentioned above, the electrostatic shield of the present invention serves to isolate the electrostatic field radiated by the radiating coil in the applicator head from the loop of the shield and from the outer casing of the applicator head. By isolating the electrostatic field in this manner, the creation of circulating currents within the outer loop of the shield and in the outer casing of the applicator head is significantly reduced thereby improving the operating efficiency thereof.

It is therefore an object of the present invention to provide an improved electrostatic shield which is arranged to substantially reduce the intensity of the circulating currents created within the various components of the shield.

Another object of the present invention is to provide an improved electrostatic shield which is arranged to effectively isolate the electrostatic field radiated by the shield's associated applicator head from the outer casing of the applicator head.

A further object of the present invention is to provide an improved electrostatic shield of the character described which is operable to reduce power loss within the applicator head and to thereby improve the operating efficiency of the diathermy apparatus.

A further object of the present invention is to provide an improved electrostatic shield of the character described which is operable to eliminate excess heating of the outer casing of the applicator head.

An additional object of the present invention is to provide an improved electrostatic shield of the character described which is arranged to virtually eliminate electrostatic (capacitive) coupling between the radiating coil within an applicator head and a load within the radiating region of the head.

A further object of the present invention is to provide an improved electrostatic shield of the character described which is arranged to make the reactive parameters of the applicator head less responsive to the surface characteristics of the load within the radiating region of the head thereby stablizing the operation of the diathermy apparatus.

Other and further objects of this invention will become apparent in the course of the following description.

DETAILED DESCRIPTION OF THE INVENTION

Figure 1:
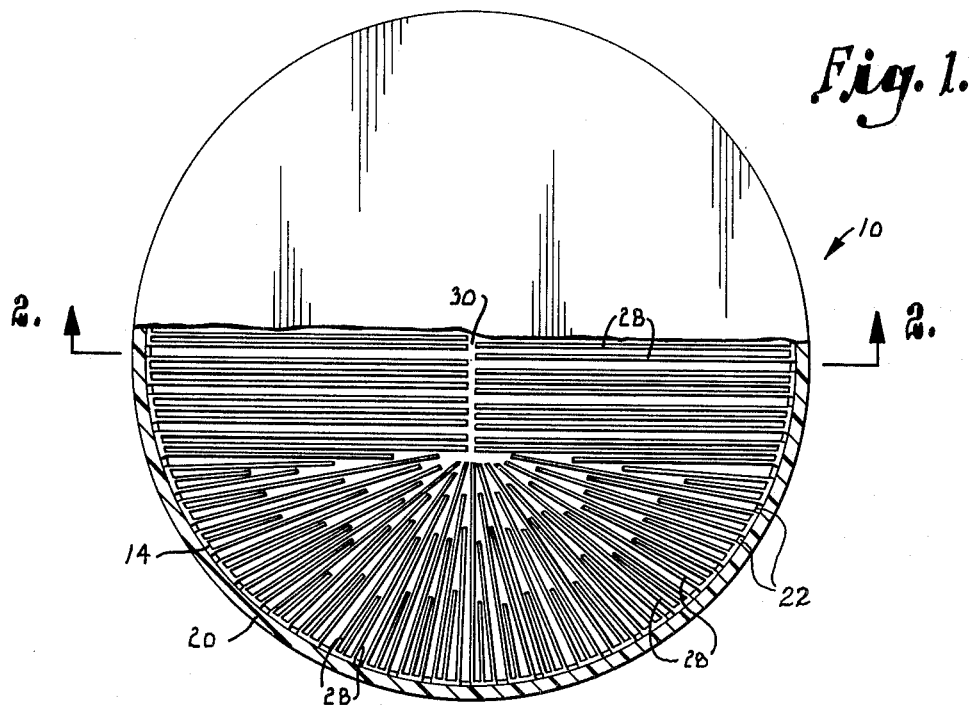
Figure 2:
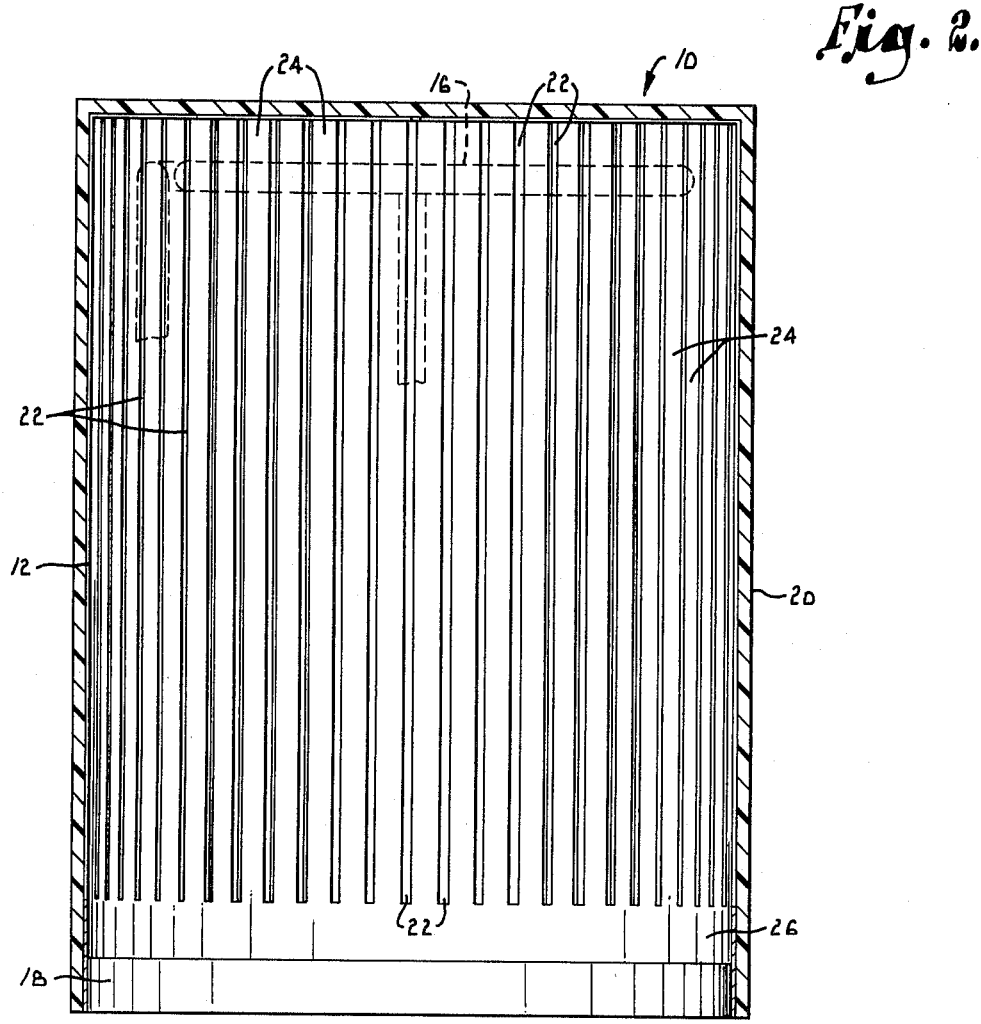

In the accompanying drawings, which form a part of the specification and are to be read in conjunction therewith, and in which like reference numerals are employed to indicate like parts in the various views:

FIG. 1 is a top plan view of an electrostatic shield which is constructed in accordance with the teaching of this invention; and FIG. 2 is a sectional view of the shield taken along line 2—2 of FIG. 1.

Reference is now made to FIGS. 1 and 2 wherein the numeral 10 is used to generally designate an electrostatic shield which is made in accordance with a preferred embodiment of the present invention. The shield 10, shown in these figures, is constructed for use on an applicator head having a circular configuration and as a result is comprised of a cylindrically shaped side portion 12 and a face portion 14. The electrostatic shield 10 of the present invention is arranged to be mounted to a diathermy applicator head such that the face portion of the shield is in a substantially parallel relationship to the plane formed by the current carrying coil in the applicator head. Such a current carrying coil is shown in FIG. 2 in broken lines and is designated by the numeral 16. The applicator head also includes a metal base plate 18 and a rigid non-conductive outer casing 20. The casing (20) may be eliminated if the shield is sufficiently rigid.

It should be noted at this time that the disclosure of an electrostatic shield for use on a "circular" applicator head is merely illustrative and should not be interpreted in a limiting sense. In fact, the configuration of the shield may be changed to accommodate an applicator head having any desired configuration. This modification is made by constructing the face portion of the shield to have a configuration which conforms to the shape of the applicator head and then extending the strips which form the side portion of the shield downward around the radiating electrodes in the head from the outer periphery of the face portion of the shield.

The side portion 12 of the shield is comprised of a copper cylinder having a plurality of slots (such as 22) cut therein to provide a plurality of lateral strips 24. The slots 22 cut in the side portion of the shield extend from the outer ridge of the side portion to a point just above the inner edge of the side portion so as to form a terminating band 26.

In the preferred embodiment of the invention, the side portion of the shield is constructed to have a length at least equal to the diameter of the heads radiating coil 16. In fact, it is sometimes desirable to extend the length of the side portion of the shield even longer to thereby decrease the magnitude of the circulating currents induced within the loop by the electromagnetic field radiated by the current carrying coil of the applicator head. While it is desirable to position this loop as far away from the coil as possible, it is impractical to make the head too long and the magnitude of the circulating currents is negligible if the shield is constructed so that the distance between the terminating band 26 and the coil 16 is at least equal to the diameter of the coil. In addition, the face portion of the shield is spaced away from the current carrying coils 16 of the head by a distance sufficient to prevent arching between the coil and the shield.

The face portion 12 of shield 10 is comprised of a plurality of electrically conductive strips such as 28 (preferably made of copper) which extend radially inward from the outer periphery of the face portion's surface. These electrically conductive strips 28 are affixed to a non-metallic mounting surface 20 by adhesion or by metalizing same on the non-metallic mounting surface by conventional etching techniques.

As shown in FIG. 1, the strips 28 which make up the face portion of the shield extend radially inward from the outer periphery of the surface defined by the face portion of the shield toward the open center area 30 of the shield. It is significant to note that the width of the strips is very small in proportion to the wave length of the energy emitted by the associated diathermy equipment to thereby minimize the introduction of circulating currents therein. While the exact configuration of the strips 28 is not essential, it is preferable to maximize the amount of surface area covered by the strips.

The outer end of each of the strips 28 is electrically coupled with an associated lateral strip 24. Each strip 28 is preferably coupled with one of the lateral strips such that it acts as a continuation of the lateral strip to which it is attached. However as shown, three of the strips 28 are connected to one lateral strip 24 for rigidity purposes only. The vertical strips 24 and face forming strips 28 may be soldered to each other, be formed in a continuous strip by an etching process or maybe otherwise coupled to provide the electrical connection therebetween. The inner end of each of the strips terminates within the inner area of the surface defined by the face portion of the shield so as to provide an open center area 30. The strips 28 are positioned to avoid contact with each other to thereby eliminate the "shorted turn" effect. If, for example, two of the strips were in an electrical engagement induced currents in the strips from the magnetic field would result. Power needed to create these induced currents would result in an energy loss which reduced the operating efficiency of the diathermy apparatus.

In use, the electrostatic shield 10 of the present invention is suitably mounted onto the applicator head such that the head's radiating coil 16 is located within the chamber formed by the side and face portion of the shield. In particular, the shield 10 is mounted onto the applicator head such that the side portion 12 of the shield encircles the head's radiating electrode and such that the face portion 14 of the shield is positioned forwardly of the radiating coil in a parallel relationship therewith.

Once the shield 10 is mounted onto the applicator head, RF energy is applied to the radiating coil causing it to radiate electrostatic and electromagnetic energy. The electrostatic energy thus radiated is effectively attenuated by the electrostatic shield 10 while the electromagnetic energy passes through the shield unimpeded. The applicator head is positioned to direct the radiated electromagnetic energy to the body tissues to be treated Since the side portion 12 of the shield 10 is slotted to provide a plurality of lateral side strips 24, the electromagnetic field energy does not produce circulating currents within the side portion of the housing. In addition, the terminating band 26 is positioned sufficiently far away from the radiating coil that the circulating currents produced therein are negligible. In this way, the electrostatic shield of the present invention is capable of effectively isolating the electrostatic energy radiated by radiating coil of the applicator head from external loads without the resultant production of excessive circulating currents within the outer casing of the head or the terminating band of the shield.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described my invention, I claim:

1. An electrostatic shield for use with a shortwave diathermy apparatus having a diathermy applicator head, said shield adapted to be placed between the diathermy applicator head having a current carrying coil located therein and the body of the patient being treated, said shield comprising:
   a first plurality of electrically conductive strips which are arranged to substantially surround said current carrying coil; and
   a second plurality of electrically conductive strips wherein each of said second plurality of electrically conducted strips is electrically coupled with one strip of said first plurality of electrically conducted strips, said second plurality of electrically conductive strips being arranged to define a plane that is substantially parallel to the plane of said coil.

2. An electrostatic shield as set forth in claim 1 including means for grounding said electrostatic shield.

3. An electrostatic shield as set forth in claim 1 including loop means for electrically coupling all of the strips of said first plurality of electrically conductive strips.

4. An electrostatic shield as set forth in claim 1 wherein the strips of said second plurality of electrically conductive strips extend radially inward from the first plurality of electrically conductive strips.

5. An electrostatic shield as set forth in claim 1 wherein a central area is defined by the strips of said second plurality of electrically conductive strips is not occupied by said second plurality of strips.

* * * * *